US011090219B1

(12) United States Patent
Hayman (10) Patent No.: US 11,090,219 B1
(45) Date of Patent: Aug. 17, 2021

(54) PROGRESSION-BASED KIT SYSTEM FOR MIMICKING PLASTIC SURGERY RESULTS

(71) Applicant: Hillary Hayman, Los Angeles, CA (US)

(72) Inventor: Hillary Hayman, Los Angeles, CA (US)

(73) Assignee: ELYSE ENTERPRISES LLC, Los Angeles, CA (US)

( * ) Notice: Subject to any disclaimer, the term of this patent is extended or adjusted under 35 U.S.C. 154(b) by 0 days.

(21) Appl. No.: 16/931,139

(22) Filed: Jul. 16, 2020

(51) Int. Cl.
*A61H 15/02* (2006.01)
*A61N 5/06* (2006.01)
(Continued)

(52) U.S. Cl.
CPC ......... *A61H 15/02* (2013.01); *A61H 15/0092* (2013.01); *A61K 31/07* (2013.01); *A61M 5/3298* (2013.01); *A61N 5/062* (2013.01); *A61N 5/0616* (2013.01); *A61Q 19/08* (2013.01); *A61H 2015/0014* (2013.01); *A61H 2201/10* (2013.01); *A61H 2201/105* (2013.01); *A61M 37/0015* (2013.01); *A61M 2037/0007* (2013.01); *A61M 2037/0023* (2013.01); *A61M 2037/0046* (2013.01); *A61M 2205/05* (2013.01);
(Continued)

(58) Field of Classification Search
CPC .................. A61M 2037/0023; A61M 37/0015
See application file for complete search history.

(56) References Cited

U.S. PATENT DOCUMENTS 3,641,334 A * 2/1972 Kipping ................. A45C 15/06
362/135
5,035,344 A * 7/1991 Christopher ........... B65D 43/18
220/823
(Continued)

FOREIGN PATENT DOCUMENTS

KR        2092204 B1 *  3/2020  ............. A45D 33/00

OTHER PUBLICATIONS

(540 Needles) Derma Micro Needle Titanium Roller for Acne Skin Care Kit 0.5mm, Sep. 15, 2020, ebay.com, <<https://www.ebay.com/itm/540-Needles-Derma-Micro-Needle-Titanium-Roller-for-Acne-Skin-Care-Kit-0-5mm/362590162763?var=631740040741&hash=item546c0ecf4b:g:xaAAAOSwi7ZcklvG>> (Year: 2019).*
(Continued)

*Primary Examiner* — William R Carpenter
(74) *Attorney, Agent, or Firm* — Concept IP LLP; Pejman Yedidsion (57) ABSTRACT

A kit system has a beginning level kit apparatus, an intermediate level kit apparatus, and an advanced kit apparatus. The beginning level kit apparatus has a first derma roller having a head with a plurality of needles each having a length of five tenths millimeters situated thereon. Additionally, the beginning level kit apparatus has a first chemical compound comprising vitamin $A_1$ at a first potency. The beginning level kit apparatus also has a first red light therapy device that that is configured to emit red light having a wavelength in the range of six hundred ten nanometers to seven hundred nanometers for a predetermined minimum time period of ten minutes. Finally, the beginning level kit apparatus has a beginning level enclosure apparatus that that encloses the first derma roller, the first chemical compound, and the first red light therapy device.

14 Claims, 10 Drawing Sheets

(51) Int. Cl.
*A61K 31/07* (2006.01)
*A61M 5/32* (2006.01)
*A61H 15/00* (2006.01)
*A61Q 19/08* (2006.01)
*A61M 37/00* (2006.01)

(52) U.S. Cl.
CPC ... *A61M 2205/051* (2013.01); *A61M 2210/04* (2013.01); *A61N 2005/0663* (2013.01)

(56) References Cited

U.S. PATENT DOCUMENTS

| | | |
|---|---|---|
| 8,376,984 B2 | 2/2013 | James |
| 2016/0184566 A1* | 6/2016 | Ibrahim ................ A61B 5/445 604/290 |

OTHER PUBLICATIONS

5IN1 Derma Roller Skin Care Set 0.5-1-1.5-2 mm w/ Free Retinol Cream 1.75 fl oz, Sep. 15, 2020, ebay.com <<https://www.ebay.com/itm/5IN1-Derma-Roller-Skin-Care-Set-0-5-1-1-5-2-mm-w-Free-Retinol-Cream-1-75-fl-oz/171102593623?hash=item27d6826257:g:pM8AAOSwLKhb~uEb>> (Year: 2018).*

Derma Roller Kit Titanium + H/A Retinol Serum + D/B Repair Gel + Derma Clean, Sep. 15, 2020, ebay.com <<https://www.ebay.com/itm/Derma-Roller-Kit-Titanium-H-A-Retinol-Serum-D-B-Repair-Gel-Derma-Clean/332484110533?var=542772600872&hash=item4d6998e8c5:g:RG0AAOSwyZhfM2z6>> (Year: 2018).*

FDA Approved | Wireless 7 Color LED Face Mask | DermRenew LED Photon Mask with 540 Titanium Micro Needle Derma Roller, Sep. 15, 2020, amazon.com <<https://www.amazon.com/DermRenew-Wireless-Titanium-Protective-Reusable/dp/B07W8VQ8DN>> (Year: 2019).*

Youyaner, How to Choose the Best Derma Roller Needle Size, DermaRollerInfo.com, Sep. 15, 2020, <<dermarollerinfo.com/derma-roller-needle-size/>> (Year: 2016).*

Clementoni, Photodynamic Photorejuvination of the Face with a Combination of Microneedling, Red Light, and Broadband Pulsed Light, 2010, Lasers in Surgery and Medicine 42: 150-159 (Year: 2010).*

Revive, Can You Use Retinol with Red Light Therapy?, Revive Light Therapy Feb. 28, 2020, <<https://revivelighttherapy.com/blog/can-use-retinol-led-light-therapy-products-together/>> (Year: 2020).*

* cited by examiner

FIG. 6B and in which:

PROGRESSION-BASED KIT SYSTEM FOR MIMICKING PLASTIC SURGERY RESULTS

BACKGROUND

1. Field

This disclosure generally relates to skincare apparatuses. More particularly, the disclosure relates to a system for mimicking plastic surgery results.

2. General Background

A plastic surgery procedure is typically performed in an office of a plastic surgeon, often at significant expense and inconvenience for those people wanting to improve the appearance of their skin. For instance, many people often have to travel far distances to obtain the services of a qualified plastic surgeon to perform the plastic surgery procedure. Although some people may elect to have a plastic surgery procedure (e.g., facelift, jaw lift, eye wrinkle reduction, etc.) to rejuvenate the appearance of their skin, others require plastic surgery to diminish or eliminate the effects (e.g., scar tissue reduction, burn minimization, etc.) from injuries. As a result, plastic surgery procedures are typically accessible only to a limited group, which may exclude those who need them most.

Furthermore, even when people undergo a plastic surgery procedure, risks are associated therewith. In some instances, those undergoing plastic surgery procedures may end up with significant disfiguration. Although the skill and experience of the plastic surgeon may play a part, other factors, such as the way the skin heals for different people, may also lead to potential disfiguration. Ultimately, plastic surgery procedures often involve significant levels of invasiveness that may injure the skin of the user.

Yet, alternative, non-invasive approaches have had questionable, if any, efficacy. For example, one alternative approach utilizes micro current technology to stimulate adenosine triphosphate ("ATP") production in an attempt to create collagen and elastin to provide a lifted appearance of the skin. However, this approach appears to have results that do not mirror plastic surgery results. Another approach may utilize radio frequency ("RF") emissions in conjunction with micro current emissions, but this approach may lead to results that worsen the skin, such as excessive redness. Yet another approach purports to oxygenate the skin to improve blood flow, but has led to health concerns, such as a racing heart, chest pressure, and light headedness.

Accordingly, current skincare configurations suffer from procedures that are too invasive (i.e., plastic surgery procedures that are costly, inconvenient, and vulnerable to possible disfiguration) or too non-invasive (i.e., devices that solely rely on technologies that emit electricity, radio waves, air, or the like above the surface of the skin of a person).

SUMMARY

In one embodiment, a kit system has a beginning level kit apparatus, an intermediate level kit apparatus, and an advanced kit apparatus.

The beginning level kit apparatus has a first derma roller having a head with a plurality of needles each having a length of five tenths millimeters situated thereon. Additionally, the beginning level kit apparatus has a first chemical compound comprising vitamin $A_1$ at a first potency (e.g., 0.3% pure Retinol). The beginning level kit apparatus also has a first red light therapy device that that is configured to emit red light having a wavelength in the range of six hundred ten nanometers to seven hundred nanometers for a predetermined minimum time period of ten minutes. Finally, the beginning level kit apparatus has a beginning level enclosure apparatus that encloses the first derma roller, the first chemical compound, and the first red light therapy device.

Furthermore, the intermediate level kit apparatus has a second derma roller having a head with a plurality of needles each having a length of one millimeter situated thereon. Additionally, the intermediate level kit apparatus has a second chemical compound comprising vitamin $A_1$ at a second potency (e.g., 0.5% pure Retinol) that is greater than the first potency. The intermediate level kit apparatus also has a second red light therapy device that that is configured to emit red light having a wavelength in the range of six hundred ten nanometers to seven hundred nanometers for a predetermined minimum time period of ten minutes. Finally, the intermediate level kit apparatus has an intermediate level enclosure apparatus that encloses the second derma roller, the second chemical compound, and the second red light therapy device.

In addition, the advanced level kit apparatus has a third derma roller having a head with a plurality of needles each having a length of one and one half millimeters situated thereon. Additionally, the advanced level kit apparatus has a third chemical compound comprising vitamin $A_1$ at a third potency (e.g., 1.0% pure Retinol) that is greater than the second potency. The advanced level kit apparatus also has a third red light therapy device that that is configured to emit red light having a wavelength in the range of six hundred ten nanometers to seven hundred nanometers for a predetermined minimum time period of ten minutes. Finally, the advanced level kit apparatus has an advanced level enclosure apparatus that encloses the third derma roller, the third chemical compound, and the third red light therapy device.

BRIEF DESCRIPTION OF THE DRAWINGS

The above-mentioned features of the present disclosure will become more apparent with reference to the following description taken in conjunction with the accompanying drawings wherein like reference numerals denote like elements and in which.

DETAILED DESCRIPTION

A progression-based kit system is provided to allow users to implement a three-step process through various stages of skincare rejuvenation. Through either multiple kits, each corresponding to a skincare rejuvenation level (e.g., beginner, intermediate, and advanced), or a single kit, which has some components that correspond to the skincare rejuvenation level, the progression-based kit system allows users to perform skincare rejuvenation at a pace that is most comfortable for them, and within the convenience of their own home. The skincare rejuvenation level may be determined according to a variety of factors (e.g., skin type, skin sensitivity, age, experience, etc.). As the user's skin improves, the user may advance to different skincare rejuvenation levels by using modified or different components.

The progression-based kit system allows a user to implement the same three-step process at each skincare rejuvenation level, with some or no adaptations to the same components. In particular, the three-step process provides users with skincare rejuvenation that mimics plastic surgery results, without users having to undergo conventional plastic surgery procedures within a plastic surgeon's office. The three-step process has been discovered to yield results that were not readily predictable; such results mimic the effects of various plastic surgery procedures (e.g., facelifts, jaw lifts, neck lifts, forehead lifts, lower eyelid blepharoplasty, and the like) without a user having to undergo a plastic surgery procedure at the office of a medical practitioner.

The progression-based kit system has various invasive and non-invasive devices/products, with each kit being tailored to a particular skincare rejuvenation level. A user may select from one of the kits, and then obtain accessories to advance to a different skincare rejuvenation level.

Figure 1:
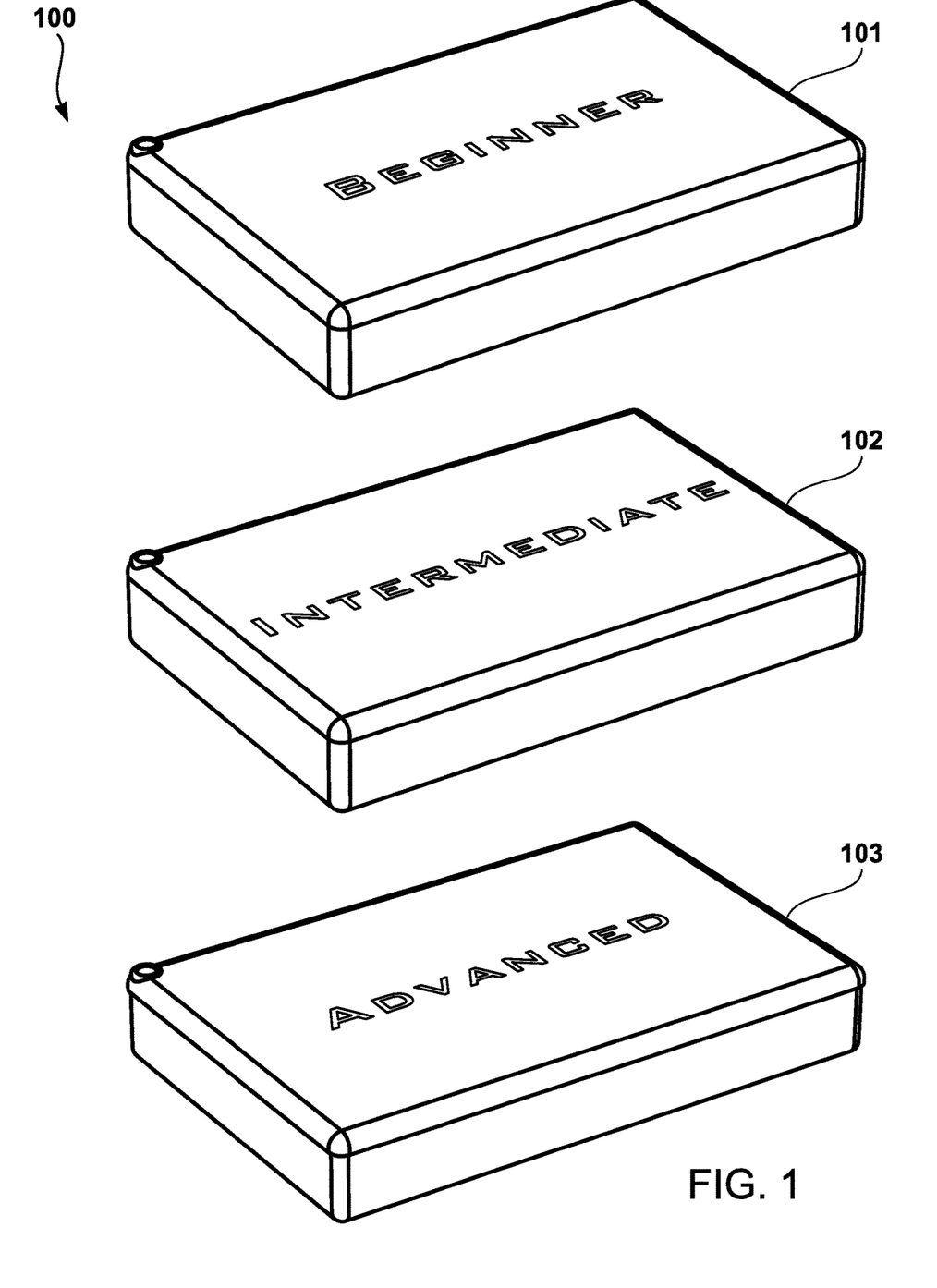
FIG. 1 illustrates a progression-based kit system, which includes a beginner kit, an intermediate kit, and an advanced kit.

FIG. 1 illustrates a progression-based kit system 100, which includes a beginner kit 101, an intermediate kit 102, and an advanced kit 103. A user may select the kit that most closely corresponds to his or her skincare rejuvenation level. For example, for a user that already has some, but not a significant amount of, experience, he or she may select the intermediate kit 102 for purchase. Each of the kits 101-103 may have all of the component devices utilized for the three-step process to allow for full application of the three-step process, irrespective of the skincare rejuvenation level at which the user begins utilizing the three-step process.

Figure 2A:
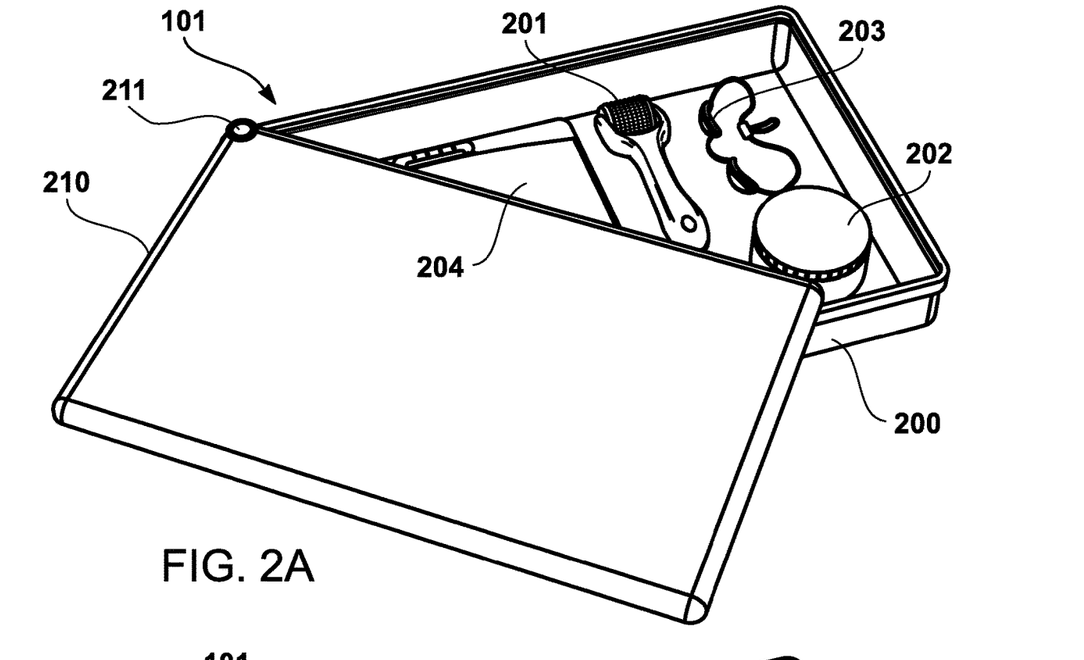
FIG. 2A illustrates the beginner kit, which encompasses a container such as a box, being opened via a swivel-based top cover, which may be operably attached to a corner, or an edge, of the top of the beginner kit.
Figure 2B:
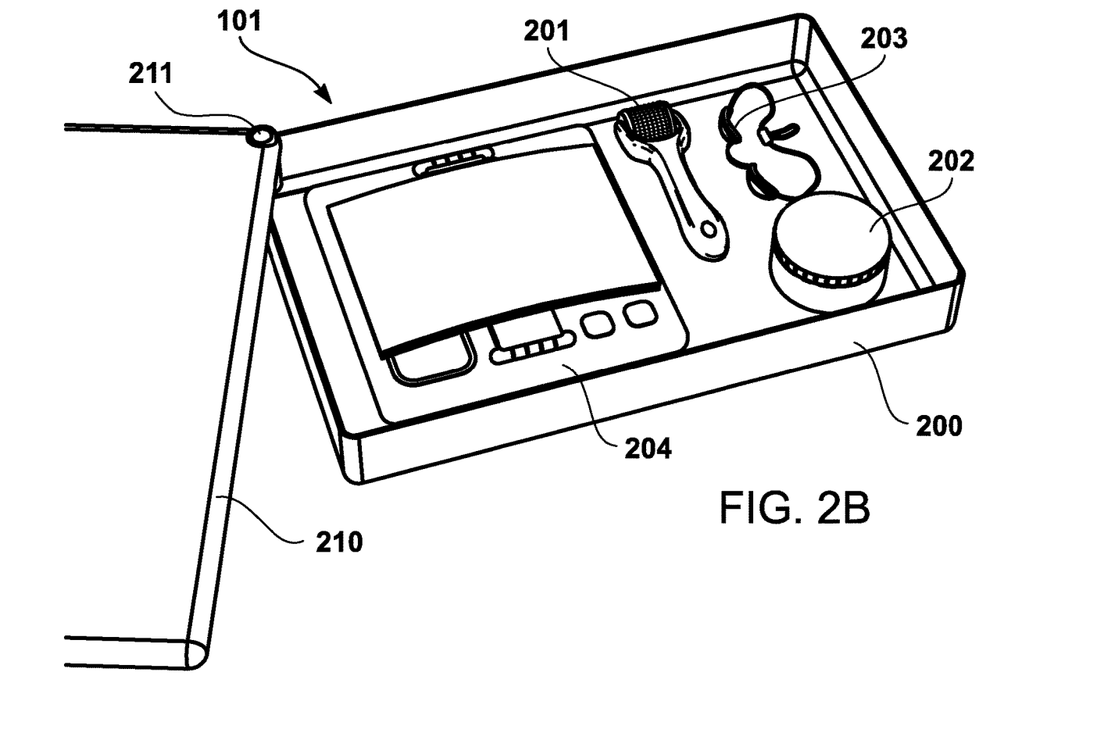
FIG. 2B illustrates the component devices of the three-step system positioned within the beginner kit prior to closure via the swivel-based top cover.
Figure 2C:
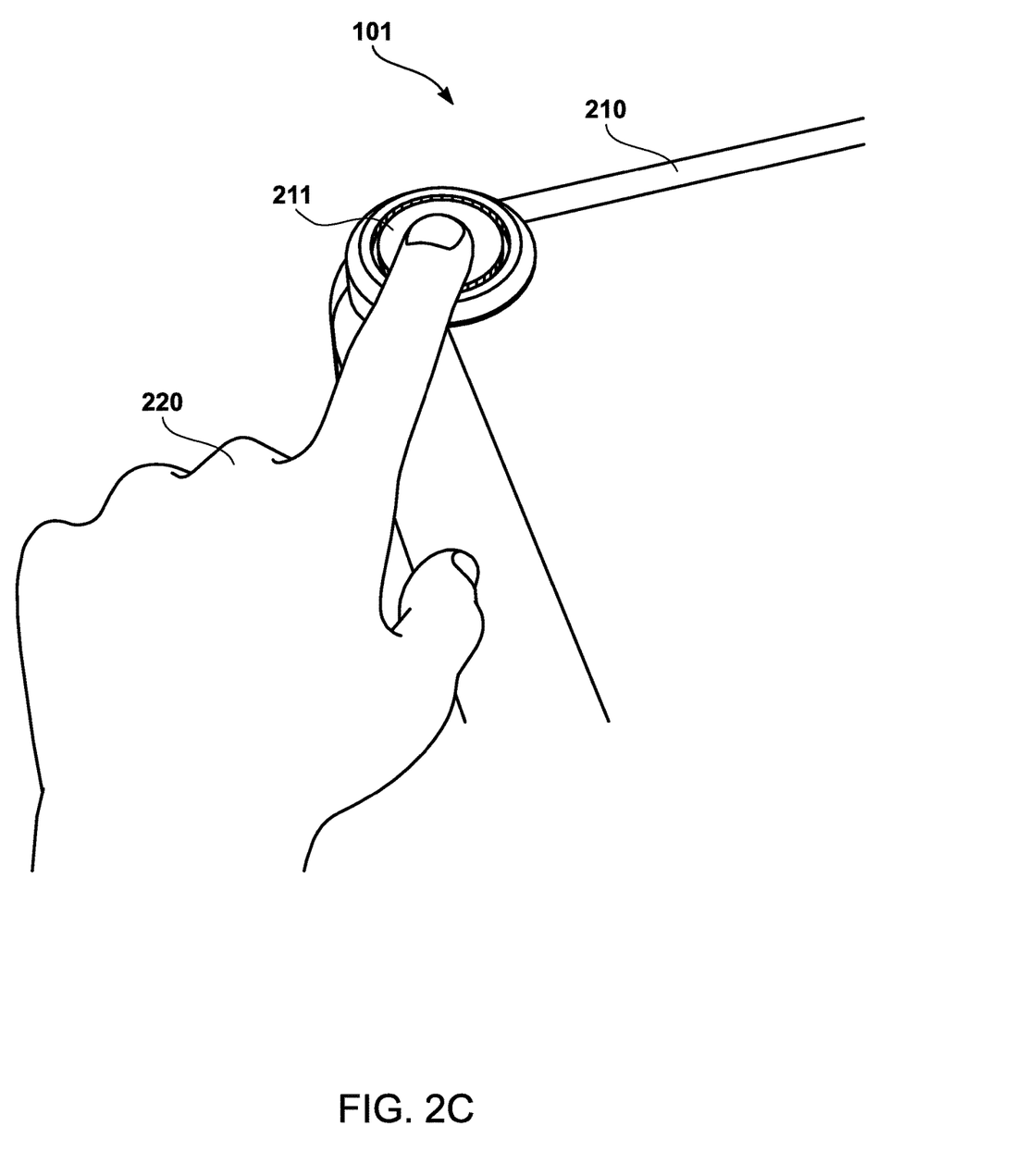
FIG. 2C illustrates the swivel-based top cover being actuated to open and/or close via an actuator button.

FIGS. 2A-2E illustrate an example of the components of the beginner kit 101. In particular, FIG. 2A illustrates the beginner kit 101, which encompasses a container 200 such as a box, being opened via a swivel-based top cover 210, which may be operably attached to a corner, or an edge, of the top of the beginner kit. (The container for the beginner kit 101 may be fabricated from a variety of durable materials, such as chrome.) The components of the beginner kit 101, corresponding to the three-step process, are also depicted for placement into the beginner kit box 200. In particular, the components include a derma roller 201, corresponding to the first step of the three-step process, a container 202 containing a chemical compound, corresponding to the second step of the three-step process, and a red light therapy machine 204 (with optional goggles for eye protection), corresponding to the third step of the three-step process. (Although the box configuration is illustrated with respect to the beginner kit 101, it may also be utilized with respect to the intermediate kit 102 or the advanced kit 103.) FIG. 2B illustrates the component devices of the three-step system positioned within the beginner kit 101 prior to closure via the swivel-based top cover 210. In one embodiment, the swivel-based top cover 210 is actuated to open and/or close via an actuator button 211, as illustrated in FIG. 2C, that may be positioned on the exterior of the beginner kit box 200. In an alternative embodiment, the swivel-based top cover 210 may be opened or closed manually.

Various component placement methodologies may be utilized for the beginner kit 101. For example, as illustrated in FIG. 2B, the derma roller 201 and the chemical compound container 202 may be positioned in proximity to the red light therapy machine 204. Stuffing material may be utilized to minimize movement of the components within the beginner kit box 200. Alternatively, the beginner kit box 200 may have one or more moldings that are configured to receive each of the components of the three-step system.

Figure 2D:
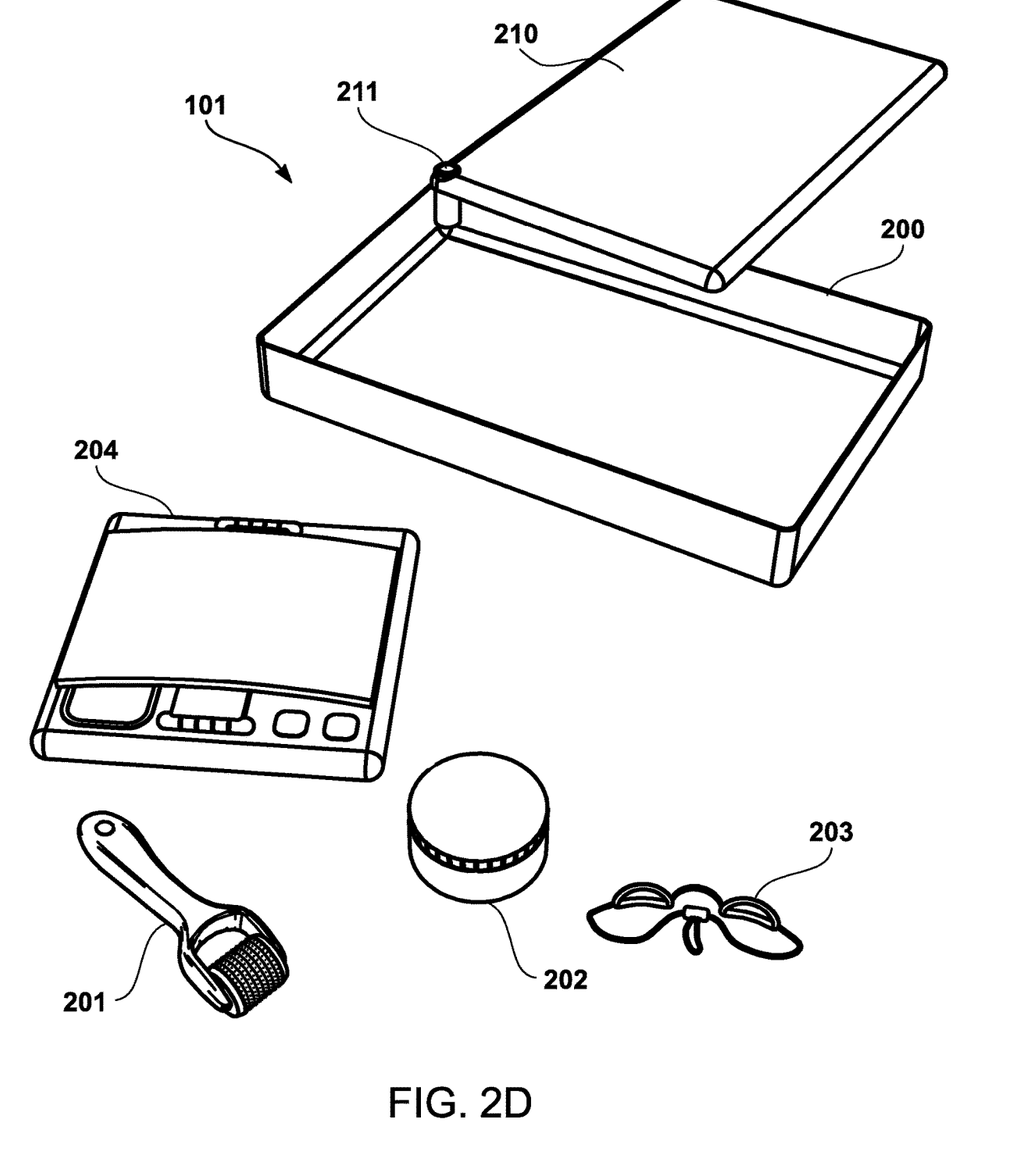
FIG. 2D illustrates the various components removed from the beginner kit box.
Figure 2E:
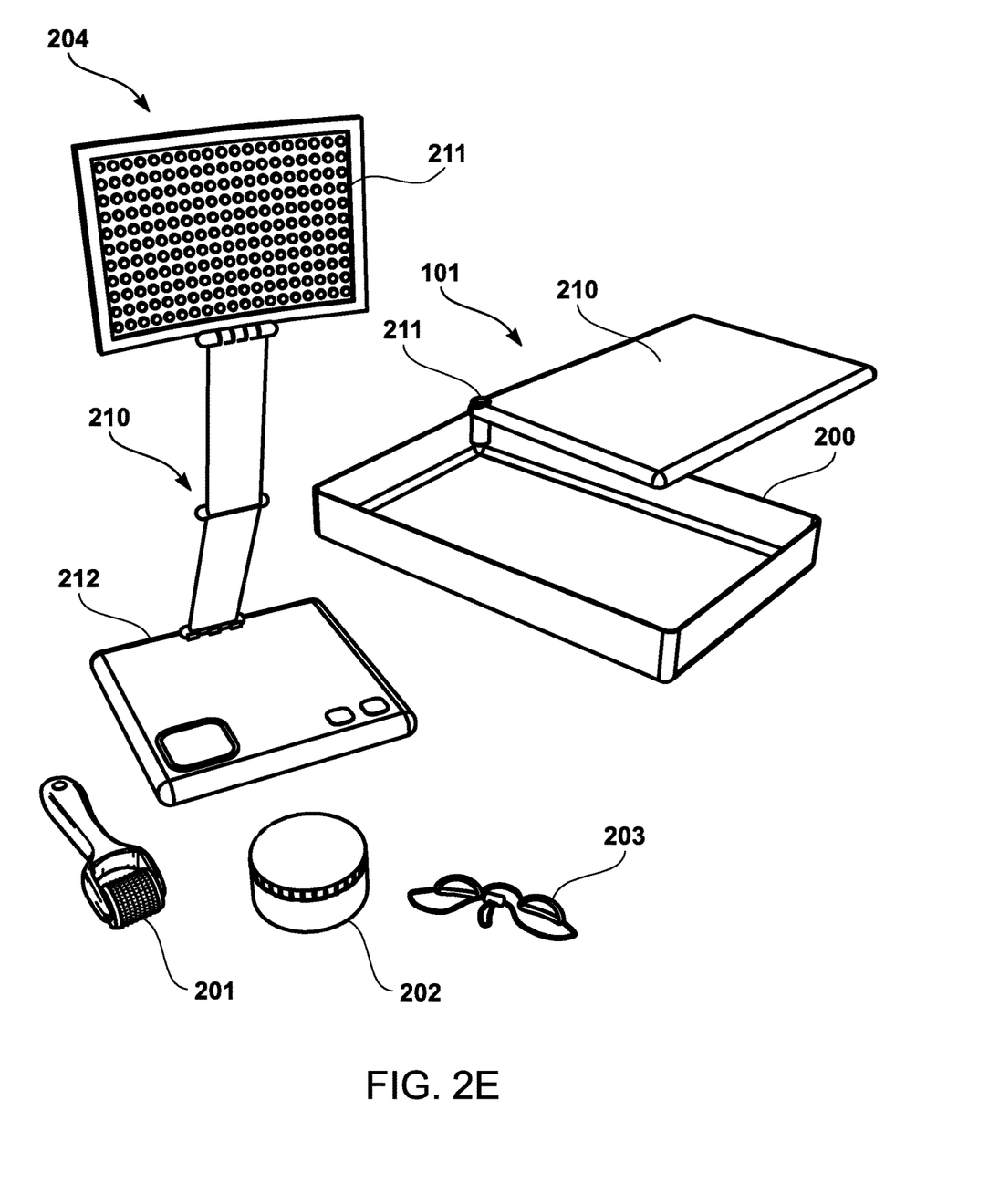
FIG. 2E illustrates the various components with the red light therapy machine in extended/un-retracted/uncompressed form.

FIG. 2D illustrates the various components removed from the beginner kit box 200. In particular, FIG. 2D illustrates the derma roller 201, the chemical compound container 202, the red light therapy machine 204, and the red light therapy goggles 203. FIG. 2E illustrates the various components with the red light therapy machine 204 in extended/unretracted/uncompressed form.

In one embodiment, the red light therapy machine 204 may have a foldable/retractable/telescopic stand 210 that may be compressed when inside the beginner kit box, and extended when outside of the beginner kit box 200. For example, the red light therapy machine may have a light emitting diode ("LED") panel 211 that is folded via hinges toward a base 212 to fit within the beginner kit box 200.

Figures 3A, 3B:
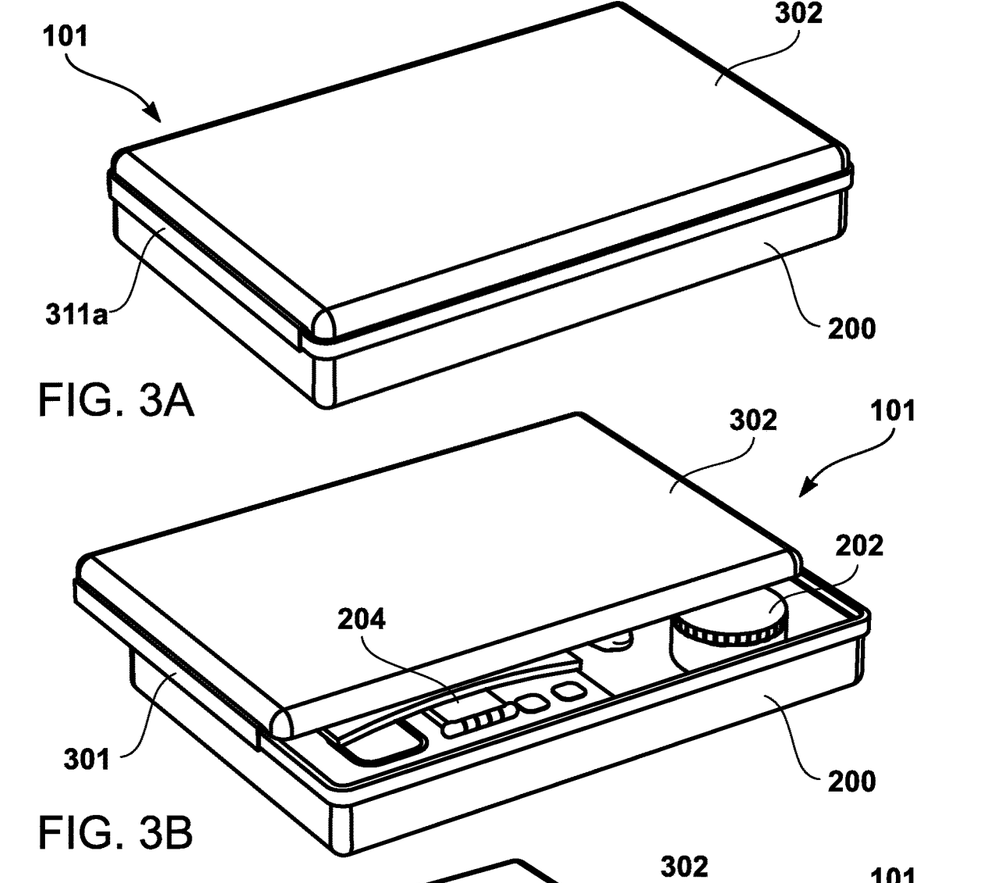
FIG. 3A illustrates a slide-based top cover that moves about one or more rails.
FIG. 3B illustrates the component devices of the three-step system positioned within the beginner kit after opening the slid-based top cover.
Figure 3C:
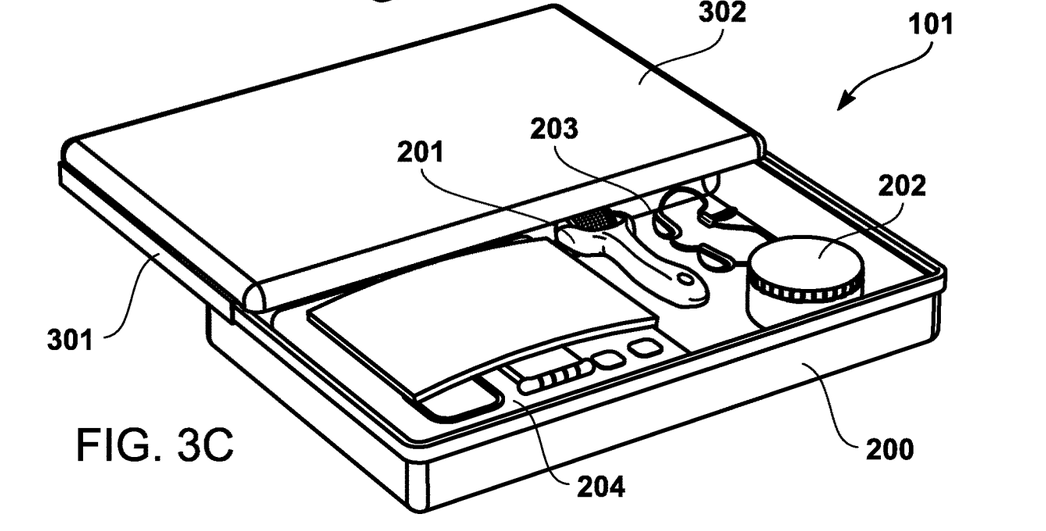
FIG. 3C illustrates the slide-based top cover being fully opened to access the components therein.

FIGS. 3A-3C illustrate a slide-based version of the beginner kit box 200. In particular, FIG. 3A illustrates a slide-based top cover 302 that moves about one or more rails 301. In particular, a plurality of rails 301 may receive edges of the slide-based top cover 302, allowing for a sliding motion to open the top cover 310. FIG. 3B illustrates the component devices of the three-step system positioned within the beginner kit 101a after opening the slid-based top cover 302. In one embodiment, an actuator (e.g., spring loaded button) may be utilized to automatically slide the top cover open and/or closed. Finally, FIG. 3C illustrates the slide-based top cover being fully opened to access the components therein.

Figure 4A:
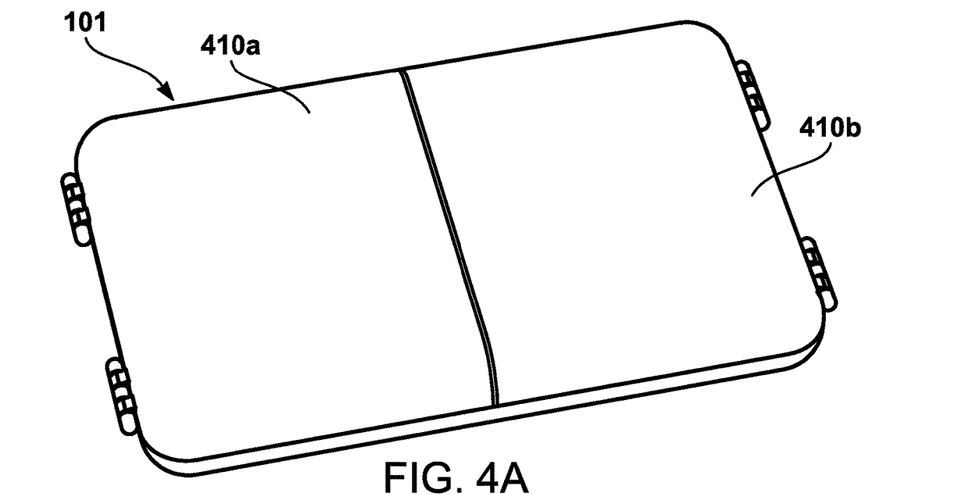
FIG. 4A illustrates a closed version of the hinge-based beginner kit box.
Figure 4B:
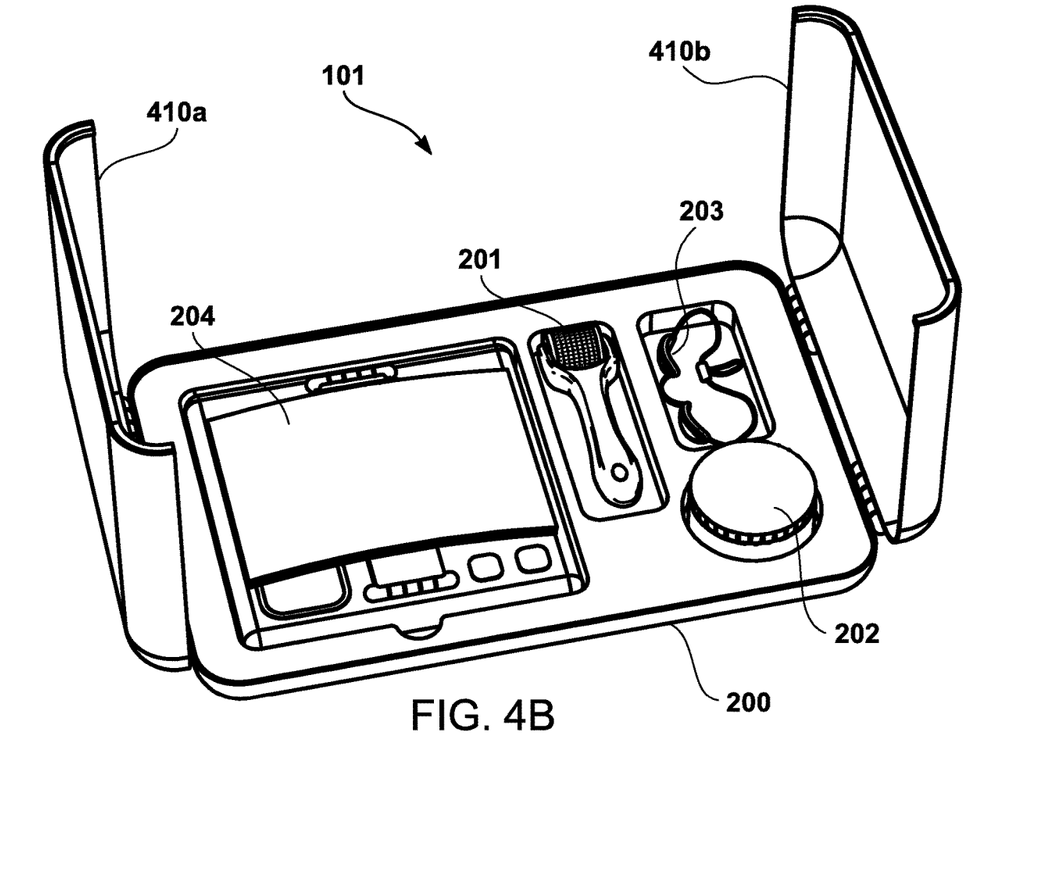
FIG. 4B illustrates the beginner kit box being partially opened to allow for access to the derma roller, the chemical compound container, the red light therapy machine, and the red light therapy goggles.
Figure 4C:
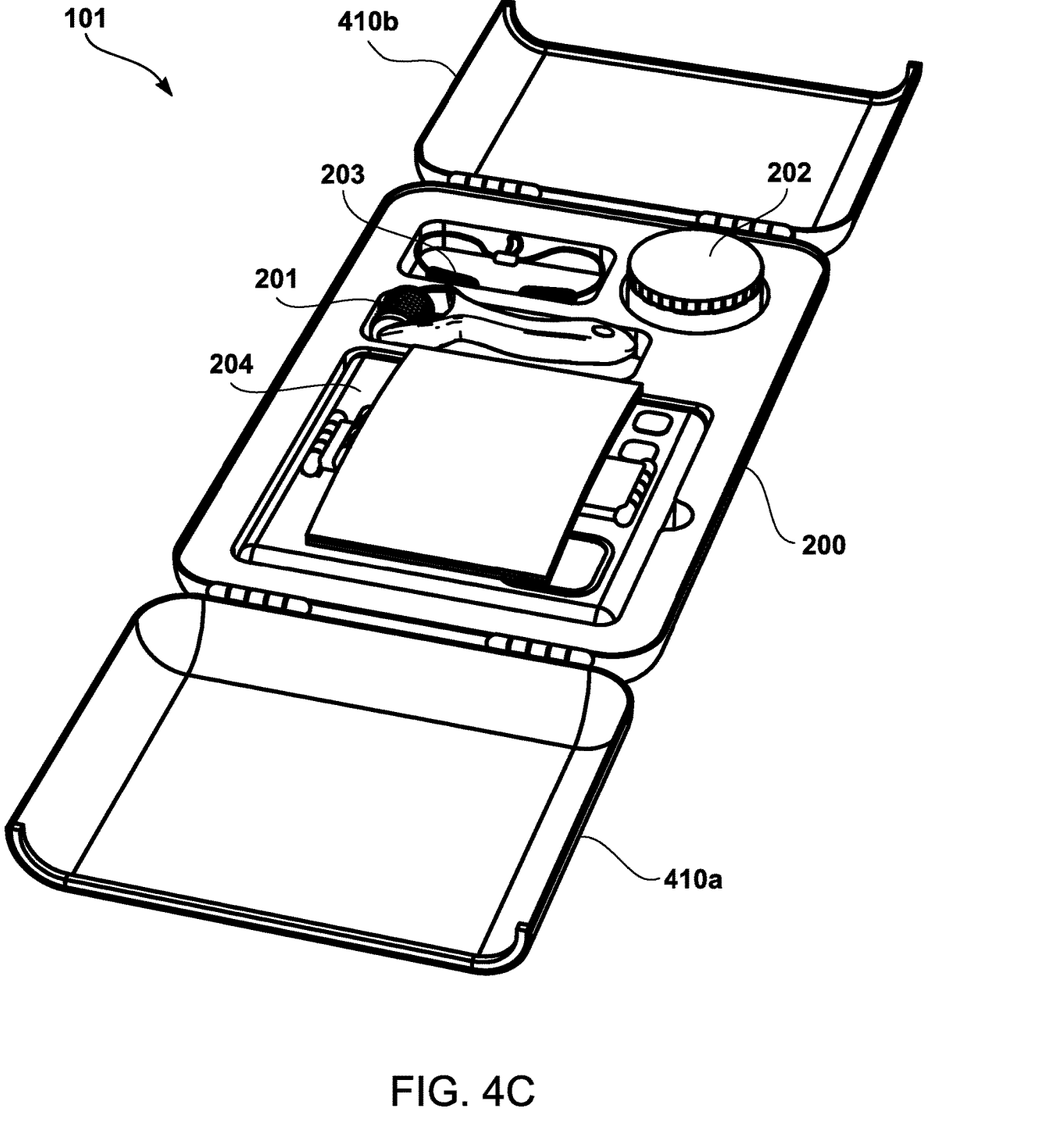
FIG. 4C illustrates the beginner kit box being fully opened via the left-hinged panel and a right hinged panel.

FIGS. 4A-4C illustrate a hinge-based version of the beginner kit box 200. In particular, FIG. 4A illustrates a closed version of the hinge-based beginner kit box 200. In particular, a left-hinged panel 410a and a right hinged panel 410b may be attached to a base of the beginner kit box 200 via hinges 410a and 410b. FIG. 4B illustrates the beginner kit box 200 being partially opened to allow for access to the derma roller 201, the chemical compound container 202, the red light therapy machine 204, and the red light therapy goggles 203. Finally, FIG. 4C illustrates the beginner kit box 200 being fully opened via the left-hinged panel 410a and a right hinged panel 410b.

Figure 5A:
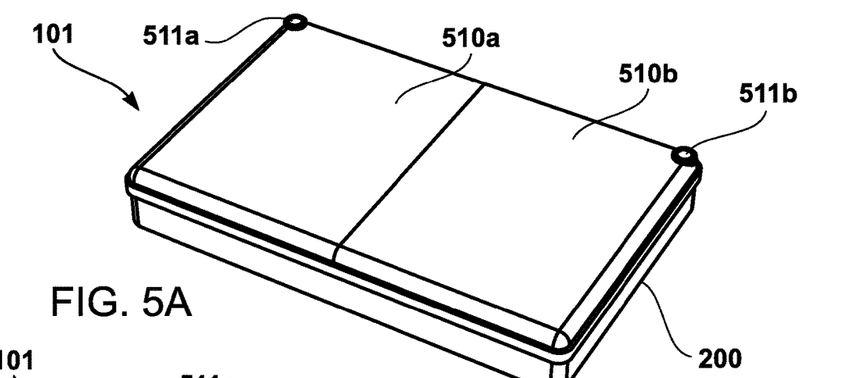
FIG. 5A illustrates a closed version of the multi-panel swivel-based version of the beginner kit box.
Figure 5B:
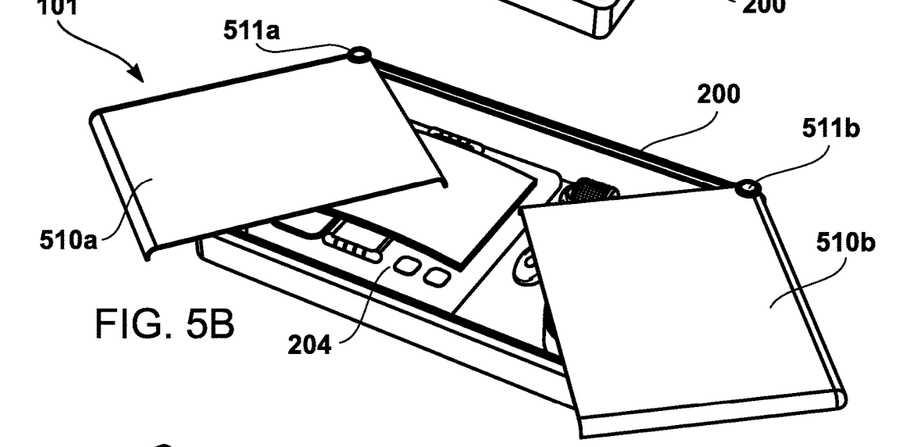
FIG. 5B illustrates a left swivel-based panel and a right swivel-based panel that may be swiveled outward via a left swivel actuator and a right swivel actuator, respectively, as illustrated in FIG. 5B.
Figure 5C:
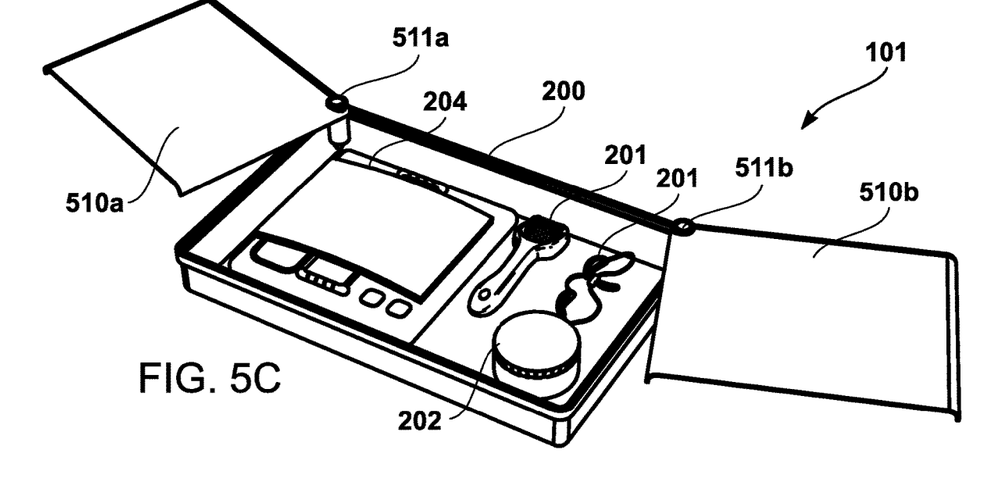
FIG. 5C illustrates the beginner kit box being fully opened via the left swivel-based panel and a right swivel-based panel.

FIGS. 5A-5C illustrate a multi-panel swivel-based version of the beginner kit box 200. In particular, FIG. 5A illustrates a closed version of the multi-panel swivel-based version of the beginner kit box 200. A left swivel-based panel 510a and a right swivel-based panel 510b may be swiveled outward via a left swivel actuator 511a and a right swivel actuator 511b, respectively, as illustrated in FIG. 5B. Furthermore, FIG. 5C illustrates the beginner kit box 200 being fully opened via the left swivel-based panel 510a and a right swivel-based panel 510b.

Figure 6A:
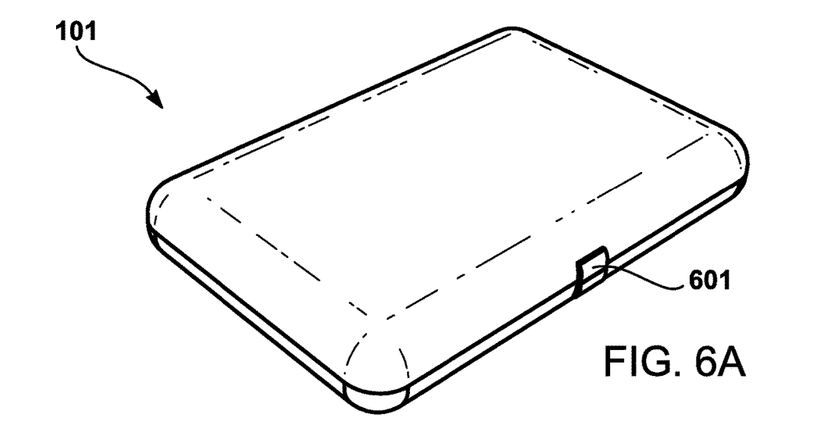
FIG. 6A illustrates the beginner kit box being closed via the latch.
Figure 6B:
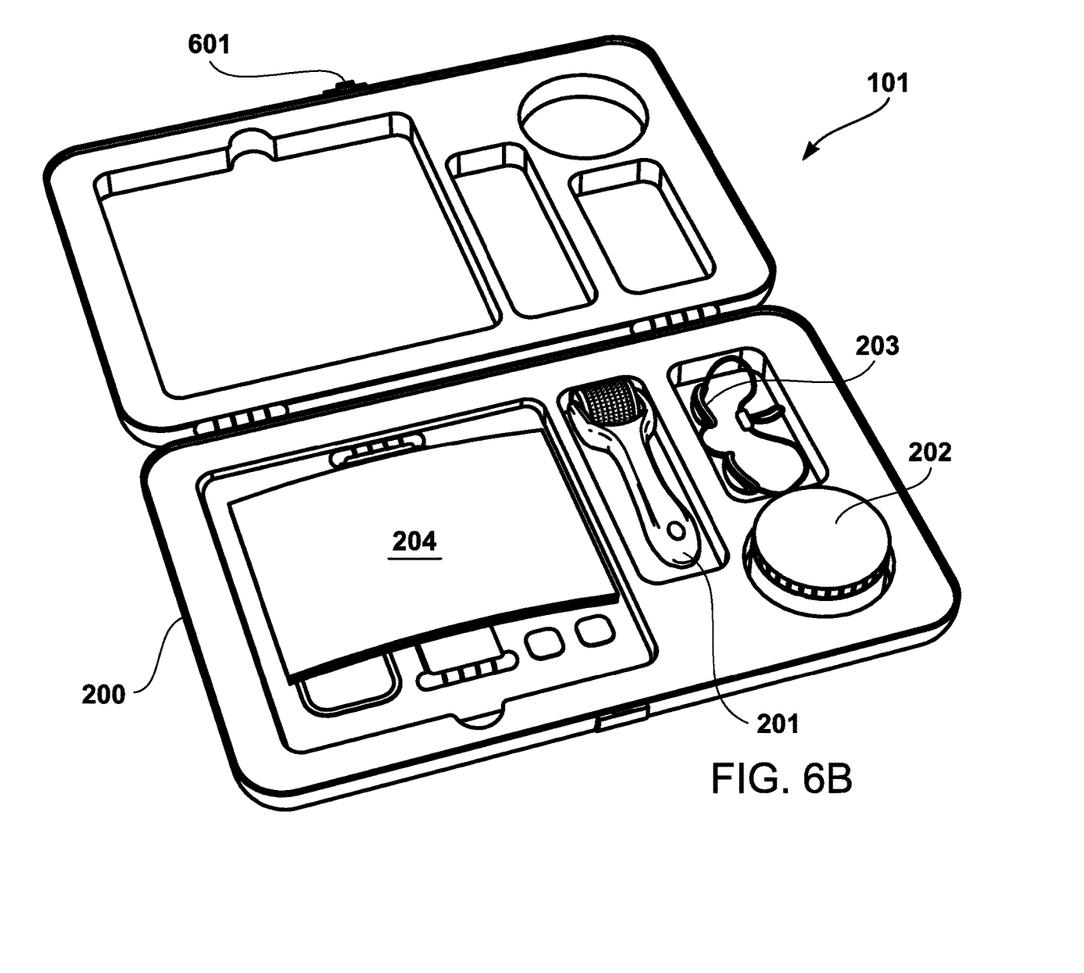
FIG. 6B illustrates the beginner kit box being opened via the latch.

As an alternative, FIGS. 6A and 6B illustrate the beginner kit box 200 being opened via a latch 601. In particular, FIG. 6A illustrates the beginner kit box 200 being closed via the latch 601. Furthermore, FIG. 6B illustrates the beginner kit box 200 being opened via the latch 601.

The beginner kit box 200 is utilized as an example for the possible box configurations, but those configurations may also be utilized as intermediate and advanced boxes.

Additionally, the shape and dimensions of the boxes illustrated herein are provided for illustrative purposes only. Other shapes and dimensions for the boxes may be utilized instead. Furthermore, other types of mechanisms (e.g., latches, buttons, clips, screws, bolts, pins, etc.) than those illustrated may be utilized to attach the cover to the box.

The progression-based kit may be utilized by a user of the three-step process to rejuvenate the user's skin. The three-step process provides users with skincare rejuvenation that mimics plastic surgery results, without users having to undergo conventional plastic surgery procedures within a plastic surgeon's office. By way of contrast, the three-step process may be performed from the convenience of one's own home, or other place of comfort.

In particular, the three-step process has been discovered to yield results that were not readily predictable; such results mimic the effects of various plastic surgery procedures (e.g., facelifts, jaw lifts, neck lifts, forehead lifts, lower eyelid blepharoplasty, and the like) without a user having to undergo a plastic surgery procedure at the office of a medical practitioner. In essence, the three-step process includes application of various invasive and non-invasive devices/products according to particular parameters to mimic plastic surgery results. Firstly, the three-step process includes usage of the derma roller 201 in the progression based kits in an area of intended rejuvenation. Particular needle lengths and movement of the derma roller has been discovered to maximize skin rejuvenation. Secondly, a chemical compound containing vitamin $A_1$ (e.g., Retinol), positioned within the chemical compound container 202, is applied to the area of intended skin rejuvenation via the channels in the skin created by the derma roller. Accordingly, the chemical compound is able to reach the dermis layer of the skin, directly underneath the epidermis, much faster than would be required through prolonged exposure to the chemical compound; as a result, collagen production is increased in an optimal manner to rejuvenate (i.e., tone, tighten, and/or lift) the skin. Finally, the red light therapy device 204 is utilized to emit red light (i.e., light having a wavelength of six hundred ten nanometers to seven hundred nanometers) toward the area of intended rejuvenation, which further increases collagen production.

Accordingly, the positioning of the chemical compound within the channels created by derma roller 201, combined with the sequential step of red light emission toward the area of intended rejuvenation, has been discovered to have an enhanced collagen production effect that mimics plastic surgery results.

Furthermore, the same three-step process may be utilized in a universal manner with respect to various portions of the face to mimic plastic surgery results corresponding to different plastic surgery procedures (e.g., face lift, jaw lift, etc.), but with the same process. In other words, one process may be utilized in different zones of the face of a user to mimic plastic surgery results that would typically require different plastic surgery procedures, associated with potentially different visits to a plastic surgeon's office.

Additionally, in one embodiment, the three-step process may be utilized to simultaneously mimic the results from multiple plastic surgery procedures during one application. For example, the user may apply the derma roller to both the skin around the eyes and the skin around the jaw during one application, followed by application of retinol to the skin around the eyes and the skin around the jaw, and followed by red light therapy emission to the skin around the eyes and the skin around the jaw. Accordingly, the three-step process allows a user to simultaneously mimic plastic surgery results corresponding to multiple plastic surgery procedures at the same time, and by using the same process, without necessitating any variation thereto.

Particular needle lengths and movement of the derma roller has been discovered to maximize skin rejuvenation. The beginner kit 101 has needle lengths of 0.5 mm, the intermediate kit 102 has needle lengths of 1.0 mm, and the advanced kit has needle lengths of 1.5 mm. The skin of the face, which is more sensitive than other areas of the body, has been determined to optimally react to a needle length starting at 0.5 mm, or a length that is substantially similar thereto (e.g., within a one to thirty percent tolerance threshold). However, even for an advanced user, the skin of the face has been determined to be too sensitive to react well to a needle length of more than 1.5 mm, or a length that is substantially similar thereto (e.g., within a one to thirty percent tolerance threshold). The chemical compound is able to reach the dermis layer of the skin, directly underneath the epidermis, much faster than would be required through prolonged exposure to the chemical compound; as a result, collagen production is increased in an optimal manner to rejuvenate (i.e., tone, tighten, and/or lift) the skin. Finally, the red light therapy device 204 is utilized to emit red light (i.e., light having a wavelength of six hundred ten nanometers to seven hundred nanometers) toward the area of intended rejuvenation, which further increases collagen production. Accordingly, the positioning of the chemical compound within the channels created by derma roller, combined with the sequential step of red light emission toward the area of intended rejuvenation, has been discovered to have an enhanced collagen production effect that mimics plastic surgery results.

Upon advancing to another skincare rejuvenation level, the user may obtain kit enhancement accessories. For example, the user may order a 1.0 mm set of needles upon completing the beginner skincare rejuvenation level.

Furthermore, the progression-based kits may be categorized for particular age groups. For example, a mature progression-based kit may be specifically tailored to people over forty years old, whereas a standard progression-based kit may be specifically tailored to people that are younger. Given the different levels of skin elasticity and durability as people age, the mature progression-based kit may be utilized to have shorter needles than those of the standard progression-based kit.

Moreover, the progression-based kits may also be based on application to the body, rather than the face. Accordingly, the progression-based kits may be tailored to have longer needles than those utilized for the face, and may be utilized universally for all skincare rejuvenation levels, given the durability of the skin of the body in comparison with the face. For example, a needle length of 2.0 mm may be utilized as the needle length for the derma roller for the body, irrespective of whether the user has a skincare rejuvenation level of beginner, medium, or advanced.

It is understood that the processes, systems, and apparatuses described herein may also be applied in other types of processes, systems, and apparatuses. Those skilled in the art will appreciate that the various adaptations and modifications of the embodiments of the processes, systems, and apparatuses described herein may be configured without departing from the scope and spirit of the present processes and systems. Therefore, it is to be understood that, within the scope of the appended claims, the present processes, systems, and apparatuses may be practiced other than as specifically described herein.

I claim:

1. A kit system consisting essentially of:
    a beginning level kit apparatus consisting essentially of:
       a first derma roller having a head with a plurality of needles each having a length of five tenths millimeters situated thereon, wherein the first derma roller corresponds to a first step of a three-step process, wherein the first derma roller is configured to be used in an area of intended rejuvenation, and wherein the first derma roller is configured to create channels at the area of intended rejuvenation;
       a first chemical compound comprising vitamin $A_1$ at a first potency, wherein the first chemical compound corresponds to a second step of the three-step process, wherein the first chemical compound is configured to be applied to the area of intended rejuvenation such that the first chemical compound reaches a dermis layer of skin via the channels created by the first derma roller such that a collagen production is increased at the area of intended rejuvenation;
       a first red light therapy device that is configured to emit red light having a wavelength in the range of six hundred ten nanometers to seven hundred nanometers for a predetermined minimum time period of ten minutes, wherein the first red light therapy device corresponds to a third step of the three-step process, wherein the first red light therapy device is configured to emit red light toward the area of intended rejuvenation such that the collagen production is further increased at the area of intended rejuvenation; and
       a beginning level enclosure apparatus that encloses the first derma roller, the first chemical compound, and the first red light therapy device;
    an intermediate level kit apparatus consisting essentially of:
       a second derma roller having a head with a plurality of needles each having a length of one millimeter situated thereon, wherein the second derma roller corresponds to the first step of the three-step process, wherein the second derma roller is configured to be used in the area of intended rejuvenation, and wherein the second derma roller is configured to create channels at the area of intended rejuvenation;
       a second chemical compound comprising vitamin $A_1$ at a second potency that is greater in potency than the first potency, wherein the second chemical compound corresponds to the second step of the three-step process, wherein the second chemical compound is configured to be applied to the area of intended rejuvenation such that the second chemical compound reaches the dermis layer of skin via the channels created by the second derma roller such that the collagen production is increased at the area of intended rejuvenation;
       a second red light therapy device that is configured to emit red light having a wavelength in the range of six hundred ten nanometers to seven hundred nanometers for a predetermined minimum time period of ten minutes, wherein the second red light therapy device corresponds to the third step of the three-step process, wherein the second red light therapy device is configured to emit red light toward the area of intended rejuvenation such that the collagen production is further increased at the area of intended rejuvenation; and
       an intermediate level enclosure apparatus that encloses the first derma roller, the first chemical compound, and the first red light therapy device;
    an advanced level kit apparatus consisting essentially of:
       a third derma roller having a head with a plurality of needles each having a length of one and one half millimeters situated thereon, wherein the third derma roller corresponds to the first step of the three-step process, wherein the third derma roller is configured to be used in the area of intended rejuvenation, and wherein the third derma roller is configured to create channels at the area of intended rejuvenation;
       a third chemical compound comprising vitamin $A_1$ at a third potency that is greater in potency than the second potency, wherein the third chemical compound corresponds to the second step of the three-step process, wherein the third chemical compound is configured to be applied to the area of intended rejuvenation such that the third chemical compound reaches the dermis layer of skin via the channels created by the third derma roller such that the collagen production is increased at the area of intended rejuvenation;
       a third red light therapy device that is configured to emit red light having a wavelength in the range of six hundred ten nanometers to seven hundred nanometers for a predetermined minimum time period of ten minutes, wherein the third red light therapy device corresponds to the third step of the three-step process, wherein the third red light therapy device is configured to emit red light toward the area of intended rejuvenation such that the collagen production is further increased at the area of intended rejuvenation; and
       an advanced level enclosure apparatus that encloses the first derma roller, the first chemical compound, and the first red light therapy device.

2. The kit system of claim 1, wherein the beginning level enclosure apparatus has a first actuator configured to open a first top cover portion of the beginning level enclosure apparatus that is operably attached to a first swivel of the beginning level enclosure apparatus, the intermediate level enclosure apparatus has a second actuator configured to open a second top cover portion of the intermediate level enclosure apparatus that is operably attached to a second swivel of the beginning level enclosure apparatus, and the advanced level enclosure apparatus has a third actuator configured to open a third top cover portion of the advanced level enclosure apparatus that is operably attached to a third swivel of the advanced level enclosure apparatus.

3. The kit system of claim 1, wherein the beginning level enclosure apparatus has a first top cover portion of the beginning level enclosure apparatus that is operably attached to a first swivel of the beginning level enclosure apparatus, the intermediate level enclosure apparatus has a second top cover portion of the intermediate level enclosure apparatus that is operably attached to a second swivel of the beginning level enclosure apparatus, and the advanced level enclosure apparatus has a third top cover portion of the advanced level enclosure apparatus that is operably attached to a third swivel of the advanced level enclosure apparatus.

4. The kit system of claim 1, wherein the beginning level enclosure apparatus has a first actuator configured to open a first top cover portion of the beginning level enclosure apparatus that is operably attached to a first hinge of the beginning level enclosure apparatus, the intermediate level enclosure apparatus has a second actuator configured to open a second top cover portion of the intermediate level enclosure apparatus that is operably attached to a second hinge of the beginning level enclosure apparatus, and the advanced level enclosure apparatus has a third actuator configured to open a third top cover portion of the advanced level enclosure apparatus that is operably attached to a third hinge of the advanced level enclosure apparatus.

5. The kit system of claim 1, wherein the beginning level enclosure apparatus has a first top cover portion of the beginning level enclosure apparatus that is operably attached to a first hinge of the beginning level enclosure apparatus, the intermediate level enclosure apparatus has a second top cover portion of the intermediate level enclosure apparatus that is operably attached to a second hinge of the beginning level enclosure apparatus, and the advanced level enclosure apparatus has a third top cover portion of the advanced level enclosure apparatus that is operably attached to a third hinge of the advanced level enclosure apparatus.

6. The kit system of claim 1, wherein the beginning level enclosure apparatus, the intermediate level enclosure apparatus, and the advanced level enclosure apparatus are fabricated from chrome.

7. The kit system of claim 1, wherein the beginning level enclosure apparatus, the intermediate level enclosure apparatus, and the advanced level enclosure apparatus are square-shaped.

8. The kit system of claim 1, wherein the beginning level enclosure apparatus, the intermediate level enclosure apparatus, and the advanced level enclosure apparatus are rectangle-shaped.

9. A kit consisting essentially of:
a derma roller having a head with a plurality of needles situated thereon, wherein the derma roller corresponds to a first step of a three-step process, wherein the derma roller is configured to be used in an area of intended rejuvenation, and wherein the derma roller is configured to create channels at the area of intended rejuvenation;
a chemical compound comprising vitamin $A_1$ wherein the chemical compound corresponds to a second step of the three-step process, wherein the chemical compound is configured to be applied to the area of intended rejuvenation such that the chemical compound reaches a dermis layer of skin via the channels created by the first derma roller such that a collagen production is increased at the area of intended rejuvenation;
a red light therapy device that is configured to emit red light having a wavelength in the range of six hundred ten nanometers to seven hundred nanometers for a predetermined minimum time period of ten minutes, wherein the red light therapy device corresponds to a third step of the three-step process, wherein the red light therapy device is configured to emit red light toward the area of intended rejuvenation such that the collagen production is further increased at the area of intended rejuvenation; and
an enclosure apparatus that encloses the derma roller, the chemical compound, and the red light therapy device;
wherein the enclosure apparatus has an actuator button configured to open atop cover portion of the enclosure apparatus that is operably attached to a swivel of the enclosure apparatus.

10. The kit of claim 1, wherein the enclosure apparatus is fabricated from chrome.

11. The kit claim 1, wherein enclosure apparatus is square-shaped.

12. The kit claim 1, wherein enclosure apparatus is rectangle-shaped.

13. A method consisting essentially of:
creating channels at an area of intended rejuvenation by rolling a derma roller having a head with a plurality of needles situated thereon over the area of intended rejuvenation, wherein creating channels by rolling the derma roller corresponds to a first step of a three-step process;
applying a chemical compound comprising vitamin $A_1$ to the area of intended rejuvenation such that the chemical compound reaches a dermis layer of skin via the channels created by the derma roller such that a collagen production is increased at the area of intended rejuvenation, wherein applying the chemical compound corresponds to a second step of a three-step process;
emitting red light having a wavelength in the range of six hundred ten nanometers to seven hundred nanometers for a predetermined minimum time period of ten minutes by a red light therapy device such that the collagen production is further increased at the area of intended rejuvenation, wherein emitting the red light corresponds to a third step of the three-step process; and
wherein the derma roller, chemical compound, and red light therapy device are stored enclosed within an enclosure apparatus, wherein the enclosure apparatus has an actuator button configured to open atop cover portion of the enclosure apparatus that is operably attached to a swivel of the enclosure apparatus.

14. The method of claim 13, wherein the three-step process performed in order increases the collagen production at the area of intended rejuvenation more than if only two steps of the three-step process were performed.

* * * * *